United States Patent [19]
Yamazaki et al.

[11] Patent Number: 5,827,479
[45] Date of Patent: Oct. 27, 1998

[54] APPARATUS FOR ANALYZING A PLURALITY OF ANALYSIS ITEMS

[75] Inventors: Hajime Yamazaki, Hitachinaka; Hiroshi Mitsumaki, Mito; Tadashi Ohishi, Ibaraki-machi; Tomonori Mimura, Tomobe-machi; Taku Sakazume, Hitachinaka, all of Japan

[73] Assignee: Hitachi, Ltd., Tokyo, Japan

[21] Appl. No.: 782,928

[22] Filed: Jan. 13, 1997

[30] Foreign Application Priority Data

Jan. 19, 1996 [JP] Japan ................................. 8-007162

[51] Int. Cl.⁶ .................................................. G01N 35/02
[52] U.S. Cl. .................. 422/67; 422/63; 422/64; 422/104; 436/43; 436/50
[58] Field of Search .................. 422/63, 64, 65, 422/67, 100, 104, 105; 636/43, 47, 48, 49, 50, 55, 180

[56] References Cited

U.S. PATENT DOCUMENTS 4,276,258  6/1981  Ginsberg et al. .
4,808,380  2/1989  Minekane .
4,849,177  7/1989  Jordan .
4,970,053  11/1990  Fechtner .

FOREIGN PATENT DOCUMENTS 37 17 907   5/1987   Germany .
43 13 399   4/1993   Germany .
63-29255    2/1988   Japan .
64-65458    3/1989   Japan .
6-90212     11/1994  Japan .

Primary Examiner—Long V. Le
Attorney, Agent, or Firm—Fay,Sharpe,Beall,Fagan,Minnich & McKee

[57] ABSTRACT

A reagent containing device has an outer bottle holder and an inner bottle holder. The holders are rotated independently of each other. When an instruction for exchanging reagent bottles inside the reagent containing device is input, a first reagent bottle on the outer bottle holder and a second reagent bottle on the inner bottle holder relating to the same analysis item are positioned at an opening of a bottle exchanging area. Then the opening is opened by a sliding operation of a lid so that the first reagent and the second reagent bottles can be unloaded through the opening.

5 Claims, 8 Drawing Sheets

APPARATUS FOR ANALYZING A PLURALITY OF ANALYSIS ITEMS

BACKGROUND OF THE INVENTION

The present invention relates to an apparatus for analyzing a plurality of analysis items, and more particularly relates to an apparatus for analyzing a plurality of analysis items by utilizing reaction between samples and reagents.

In a conventional automatic analyzer, samples and reagents are poured into reaction containers arranged on a reaction line, and reaction solutions formed are measured using measuring equipment such as a photometer. The automatic analyzer of this kind employs a method in which various kinds of reagents are pipetted in order to effectively measure analysis items to be analyzed.

In the prior art of performing pipetting reagents are disclosed, for example, Japanese Patent Application Laid-Open No.64-65458 corresponding to U.S. Pat. No. 4,849,177, Japanese Patent Application Laid-Open No.63-29255 corresponding to U.S. Pat. No. 4,970,053, Japanese Patent Application Laid-Open No.6-90212 corresponding to U.S. Pat. No. 4,808,380. Among them, Japanese Patent Application Laid-Open No.64-65458 discloses that reagent packs holding a plurality of cylindrical reagent bottles in a line are provided, and the plurality of reagent packs are arranged radially on a single turn table. Japanese Patent Application Laid-Open No.63-29255 discloses that reagent cartridges having three storage compartments are radially arranged on a single rotatable carousel, and the reagent cartridges are transferred by rotating the carousel. Further, Japanese Patent Application Laid-Open No.6-90212 discloses that a single table is arranged inside an annular array of reaction cuvettes, reagent bottles are arranged in two rows on the reagent table, and reagents are dispensed from the reagent bottles on each of the rows to the reaction cuvettes using dispensers.

It is troublesome work for an operator to properly operate an automatic analyzer such as setting necessary reagent bottles, and work for exchanging used reagent bottles for new reagent bottles. For example, the number of bottles required for each of the analysis items is two and the number of analysis items is thirty-five, the settling of seventy bottles is required.

In the apparatuses of Japanese Patent Application Laid-Open No.64-65458 and Japanese Patent Application Laid-Open No.63-29255, since plural reagents for a same analysis item can be provided to a reagent table as a single pack, the burden of loading and exchanging the reagent bottles can be reduced. However, positional relationship of reagents set in the outer peripheral side of the reagent table and reagents set in the inner peripheral side of the reagent table is always fixed. In the case of the apparatus of Japanese Patent Application Laid-Open 2-90212, since two rows of reagent bottles are formed on a single reagent table, the positional relationship of the reagents set in the outer peripheral side of the reagent table and the reagents set in the inner peripheral side of the reagent table is also always fixed. In these prior arts, the following problem takes place.

In a general automatic analyzer, a pipetting position for a first reagent and a pipetting position for a second reagent on a reaction line are separated. In an analyzer for performing multi-item analysis, since plural kinds of analysis items are arranged at random on a reaction line, the combination of an analysis item positioned at a first reagent pipetting position and an analysis item positioned at a second reagent pipetting position always changes.

In each of the prior arts, since the first reagent and the second reagent on the single table are rotated together while the fixed positional relationship is being maintained, the second reagent (or the first reagent) cannot be pipetted when the first reagent (or the second reagent) is being pipetted. That is, the pipetting operation of the first reagent and the pipetting operation of the second reagent cannot be performed in parallel, and as a result the effect of analysis process for many samples is decreased.

SUMMARY OF THE INVENTION

An object of the present invention is to solve a problem in that one reagent pipetting operation cannot be performed while another pipetting operation is being performed, and to provide an analyzer in which reagent bottles in different rows can be removed from both rows at one time or the reagent bottles can be set in both rows at one time. An analyzer according to the present invention comprises a reagent containing device for containing reagents to be pipetted to a reaction container on a reaction line. The reagent containing device comprises an outer bottle holder and an inner bottle holder each of which has reagent bottle receiving positions arranged in a loop-shape, a first driving means for circularly driving the outer bottle holder, and a second driving means for circularly driving the inner bottle holder; and the analyzer further comprises a control means for positioning a first reagent bottle on the outer bottle holder and a second reagent bottle on the inner bottle holder for the same analysis item as an analysis item of the first reagent bottle at a predetermined bottle exchanging area by driving the outer and the inner bottle holders corresponding to the requesting information on removing reagent bottles.

In a preferred embodiment in accordance with the present invention, the control means positions an empty reagent bottle receiving position on the outer bottle holder and an empty bottle receiving position on the inner bottle holder at the bottle exchanging area by driving the outer and the inner bottle holders corresponding to the requesting information on receiving reagent bottles.

DESCRIPTION OF THE PREFERRED EMBODIMENTS

Figure 1:
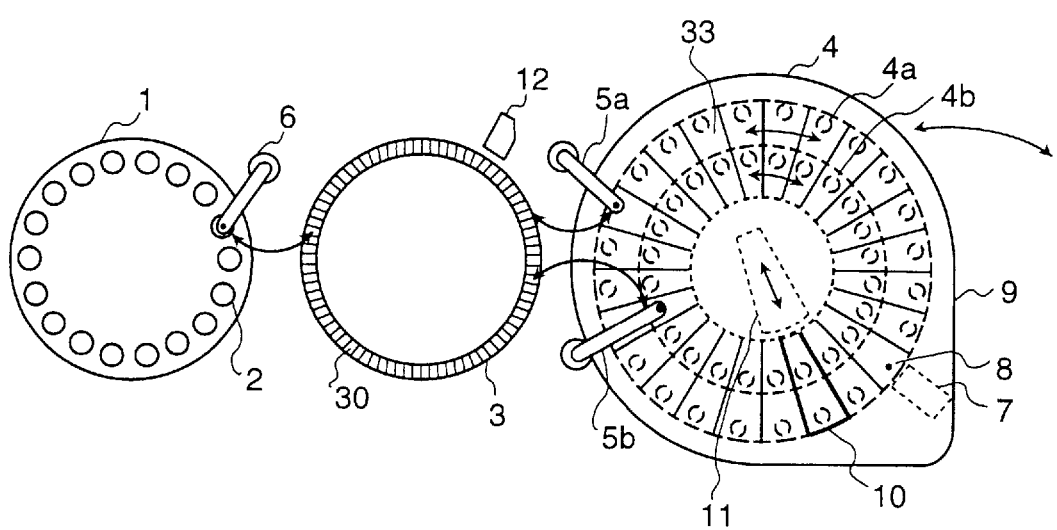
FIG. 1 is a schematic plan view showing the construction of an embodiment of an automatic analyzer in accordance with the present invention.

Referring to FIG. 1, a plurality of sample containers 2 are circularly arranged on a sample disk 1. The sample disk 1 is intermittently rotated by a drive unit, and a position on the disk 1 for each of the sample bottles 2 is detected by a well-known position detector. On a reaction disk 3, a plurality of reaction containers or reaction cuvettes 30 are circularly arranged, and a row of such reaction containers composes a reaction line. The reaction disk 3 is rotated with a predetermined time interval by a drive unit, and a position on the reaction disk 3 for each of the reaction containers is detected by a well-known position detector.

The reagent containing device 4 comprises an outer bottle holder 4a and an inner bottle holder 4b. The inner bottle holder 4b comprises a rotating table having a plurality of reagent bottle receiving positions arranged in a loop-shape. The rotating table in the inner side is rotated clockwise and counterclockwise by transmitting the driving force from a first drive unit to a rotating center shaft. The outer bottle holder 4a comprises an annular rotating table having a plurality of reagent bottle receiving positions arranged in a loop-shape. The annular table in the outer side is rotated clockwise and counterclockwise by transmitting the driving force from a second drive unit through a gear in contact to the outer periphery of the table. Each of the bottle receiving positions on the outer and the inner bottle holders 4a, 4b is detected by a well-known position detector.

A reagent bottle 33 can be mounted on each of the bottle receiving positions formed on the outer and the inner bottle holders 4a, 4b. A row of bottles in the outer periphery and a row of bottles in the inner periphery are formed by setting a plurality of reagent bottles. A length in the radial direction of the bottle receiving position in the outer bottle holder is formed larger than a length in the radial direction of the bottle receiving position in the inner bottle holder. By doing so, an inner peripheral reagent bottle can be set in the receiving position in the outer peripheral side.

Each of reagent pipetters 5a, 5b having a pipetting nozzle on its rotatable arm pipets a predetermined volume of a reagent in a reagent bottle selected from a corresponding row of the reagent bottles 33 into a reaction container on the reaction disk 3 corresponding to an analysis item. A sample pipetter 6 having a pipetting nozzle on its rotatable arm pipets a predetermined amount of a sample from a sample container to the reaction container on the reaction line.

An identifying information reading unit 7 such as a bar code reader is arranged near the outer bottle holder 4a. Reagent information such as a bar code attached on the outer surface of each of the reagent bottles is read by the reading unit 7 and transmitted to a control unit. A light transmitting portion 8 is formed in a specified position of the outer bottle holder 4a, and no reagent bottle is placed in this light transmitting portion. Reagent information of the reagent bottles on the inner bottle holder 4b is read by the reading unit 7 through the light transmitting portion 8. The number of the light transmitting portions 8 is one or more.

The outer and the inner bottle holders 4a, 4b are covered over with a movable cover 9. In an appropriate position in the movable cover 9 there is provided an opening 10 which is formed such that one reagent bottle in each of the outer and the inner side rows can be taken out. The opening 10 corresponds to the bottle exchanging area. The opening 10 is opened and closed by a slidable lid 11. Further, the movable cover 9 has nozzle entering holes so that the pipetting nozzles of the reagent pipetters 5a, 5b can enter into reagent bottles positioned at the reagent pipetting positions in the rows respectively.

The sample pipetter 6 delivers a sample in a sample container 2 to a plurality of reaction containers on the reaction desk 3 corresponding to an instructed number of analysis items. A first reagent corresponding to the analysis item is added to the reaction containers 30 using the reagent pipetter 5a to initiate the first reaction. After a predetermined time period, a second reagent corresponding to the analysis item is added to the reaction containers using the reagent pipetter 5b to initiate the second reaction. The reaction solution formed in each of the reaction containers 30 is optically analyzed by a multi-wavelength photometer 12 arranged along the reaction line.

Figure 2:
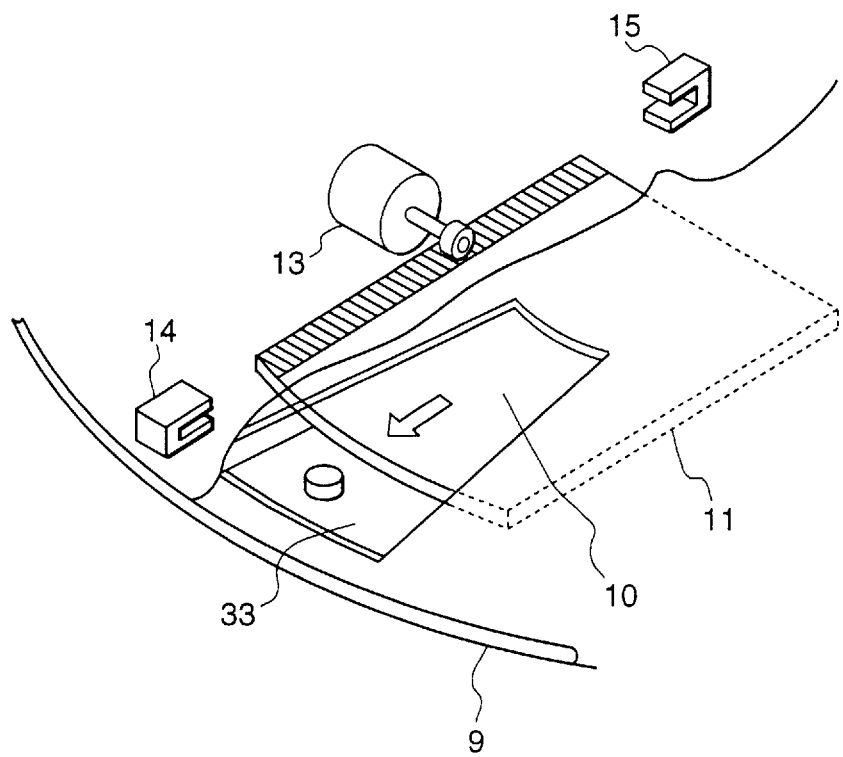
FIG. 2 is a view showing the construction near a bottle exchanging area of the analyzer of FIG. 1.

Referring to FIG. 2, the lid 11 for opening and closing the opening 10 is a plate-shaped slidable lid which is operated by a motor 13. The detector 14 is a photo-coupler for detecting a closing state of the lid 11, and the detector 15 is a photo-coupler for detecting an opening state of the lid 11. In a state where the reagent bottles are to be set to the reagent containing device 4 or where the reagent bottles are to be taken out from the reagent containing device 4, the motor 13 is operated to open the lid 11 by a command from a control unit, and thereby an operator can set the reagent bottles into both of the bottle holders 4a, 4b or take out the reagent bottles from both of the bottle holders 4a, 4b.

Figure 3:
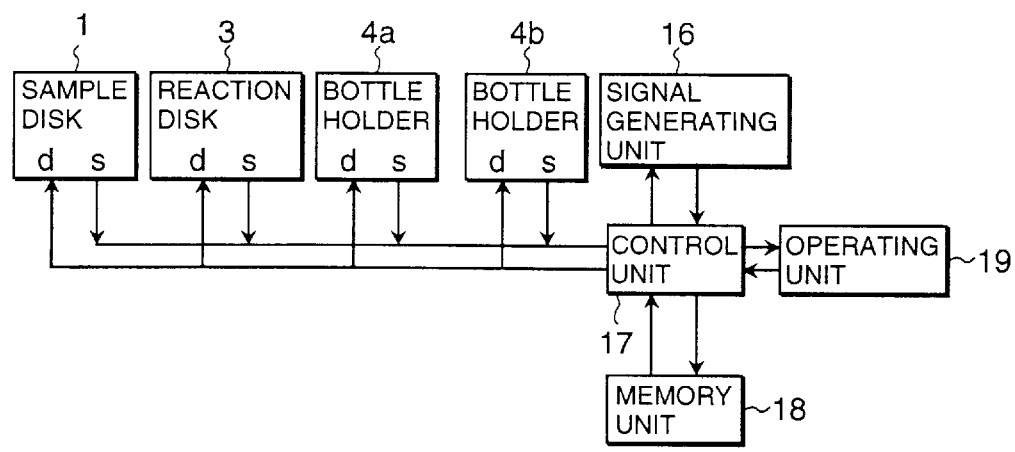
FIG. 3 is a diagram showing the system construction of the analyzer of FIG. 1.

Referring to FIG. 3, corresponding to a request from an operating unit 19, a signal generating unit 16 outputs to the control unit 17 a reagent bottle receiving request signal for notifying that reagent bottles are required to be set to the reagent containing device 4. On receiving information that a reagent in a bottle for a specified analysis item in the bottle holders 4a, 4b runs out, the signal generating unit 16 outputs a request signal to remove the reagent bottle to the control unit 17. A memory unit 18 stores reagent information on each of the bottles read by the reading unit 7 in correspondence with to position information on the receiving position of the bottle holders 4a, 4b. The sample disk 1, the reaction disk 3 and the bottle holders 4a, 4b respectively have position sensors s and driving units d and are independently rotated to required positions. Operation of these mechanisms is controlled by the control unit 17. The operator can input analysis information for each of the samples and operation request information for the reagent containing device 4.

Figure 4:
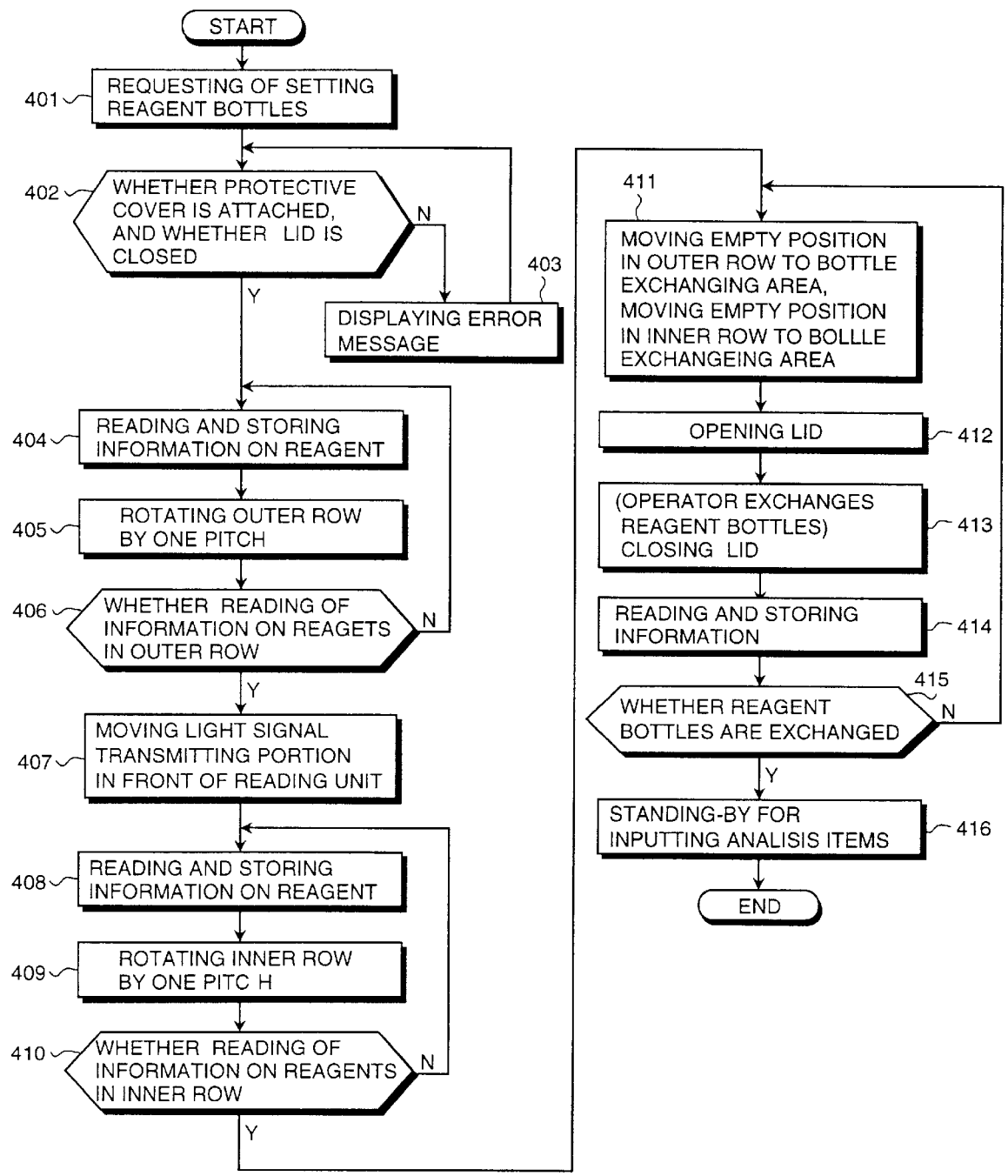
FIG. 4 is a flowchart showing an embodiment of a process when reagent bottles are set.

The operation for the case of setting reagent bottles into the reagent containing device 4 is performed according to the flow chart of FIG. 4.

Referring to FIG. 4, when the operator requests the apparatus from the operating unit 19 to set reagent bottles to the reagent containing device 4, the signal generating unit 16 generates a reagent bottle setting request signal to input it to the control unit 17 (Step 401). On receiving the setting request signal, the apparatus confirms (detects) that the protective cover 9 is attached and the lid 11 is closed (Step 402). If yes, the processing advances to Step 404. If no, the processing advances to Step 403 to display an error message. In Steps 404 to 406, the reading unit 7 reads reagent information attached on the outer surface of the reagent bottles in the row of the outer peripheral side while the outer bottle holder 4a is being rotated.

Figure 6:
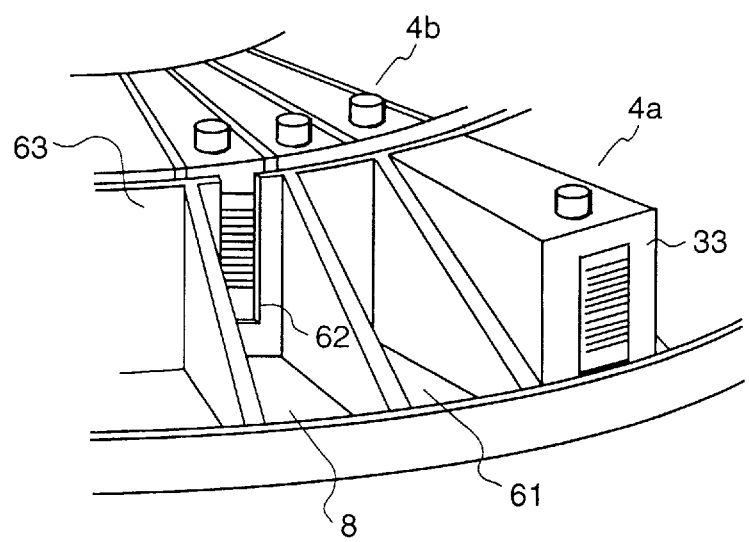
FIG. 6 is a view showing the construction near a light transmitting portion formed in an outer bottle holder.

As shown in FIG. 6, many bottle receiving positions 61 formed in the outer bottle holder 4a of the reagent containing device 4 have a wall 63 in the back. The wall 63 is high enough to hide bar codes attached on the outer surface of the reagent bottles arranged on the inner bottle holder 4b. Thereby, information on reagent bottles in the inner side row is prevented from being erroneously read. There is formed a cut-out portion 62 as a window for reading the identifying information at the light transmitting portion 8 in the back wall where the reagent bottles are not placed. The reading unit 7 can read the bar codes of the reagent bottles in the inner side row through the cut-out portion. The read reagent information is stored in the memory unit 18 together with information from the position detectors in the reagent row. The positions in which reagent bottles are not placed except for the light transmitting portion 8 are stored as empty positions.

In Step 407 of FIG. 4, in preparation for reading the reagent information of the reagent bottles in the inner peripheral row, the light transmitting portion 8 in the outer bottle holder 4a is moved to a position facing the reading unit 7 and the outer bottle holder 4a is stopped with keeping the state. While the outer side row is being stopped, the inner bottle holder 4b is rotated to read the bar codes of the reagent bottles in the inner side row through the light transmitting portion 8 by the reading unit 7, and the read reagent information is stored in the memory 18 corresponding to the positional information from the position detector s in the inner bottle holder 4b (Step 408). The inner side row is rotated by one pitch (Step 409), and the processes of Step 408 and Step 409 are repeated until all the bottles are read (Step 410). The bottle receiving positions 61 on the outer and the inner bottle holders 4a, 4b in which bottles are not placed are stored as empty positions.

Then an empty position in the outer side row and an empty position in the inner side row are matched to each other and rotated to the bottle exchanging area 10 (Step 411). After the bottle holders 4a, 4b are rotated, the lid 11 is opened (Step 412). The operator sets first reagent and second reagent bottles for the same analysis item and closes the lid 11. Soon after the apparatus confirms closing of the lid 11, both of the set reagent bottles in the outer side row and in the inner side row are rotated in front of the reagent information reading unit 7. Firstly, the reagent information of the newly set reagent bottle in the outer side row is read, and then the light transmitting portion 8 in the outer side row is rotated in front of the reagent information reading unit 7 and the reagent information of the newly set reagent bottle in the inner side row is read. The read reagent information is stored in the memory unit 18 together with the positional information (Step 414).

In an embodiment different from FIG. 4, the reagent information reading unit 7 is provided in the same place as the bottle exchanging area 10. In this case, since the time for rotating the reagent bottle in front of the reagent information reading unit 7 is not needed, the time required for setting the reagent bottles can be reduced compared to the reading method described above. That is, soon after setting the reagent bottles and closing the lid 11, the reagent information of the newly set reagent bottle in the outer bottle holder 4a is read. Then the light transmitting portion 8 provided in the outer bottle holder 4a is rotated in front of the reagent information reading unit 7 to read the reagent information on the newly set reagent bottle in the inner bottle holder 4b. The read reagent information is stored in the memory unit 18 together with the positional information. After completion of reading the pair of reagent information in regard to the same analysis item, empty positions are again rotated to the bottle exchanging area 10 and the lid 11 is opened.

Returning to FIG. 4, after completion of setting the reagent bottles (Step 415), the operator inputs the notice of completion from the operating unit 19. The apparatus receives the information and closes the lid 11, and is in a stand-by state for waiting for an analysis item and so on (Step 416). Then, the apparatus is started into operation according to an instruction.

It is not necessary that the reagent information is read every time the reagent bottles are set. For example, in the initial operation, after completion of the setting of all of the reagent bottles, firstly the outer side row is rotated to read reagent information on all of the bottles in the outer side row, and successively the light transmitting portion 8 is rotated in front of the reagent information reading unit 7 to read the reagent information of all the bottles in the inner side row while the inner side row is being rotated. The information is stored in the memory 18 together with the positional information.

Figure 5:
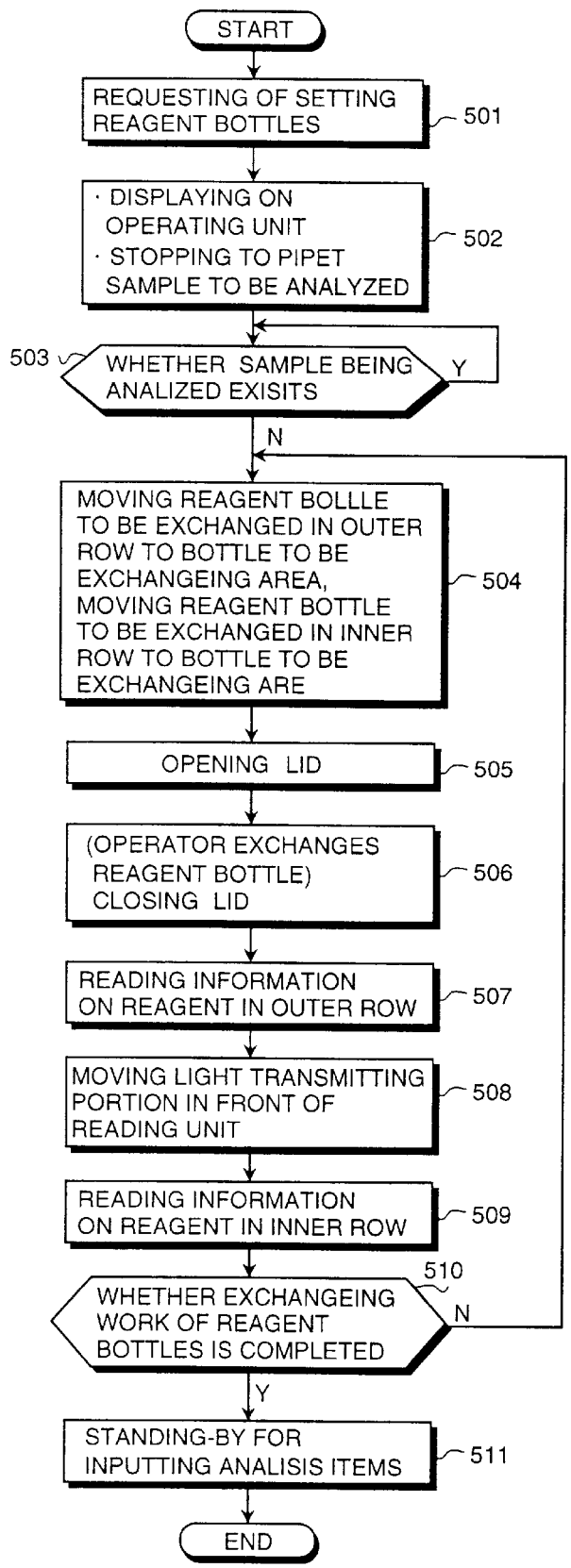
FIG. 5 is a flowchart showing an embodiment of a process when reagent bottles are exchanged.

Operation in a case where reagent bottles need to be exchanged during operation of the analysis apparatus is performed according to the flow chart of FIG. 5.

Referring to FIG. 5, when the necessity of exchanging reagent bottles arises due to the lack of a reagent during operation of the analysis apparatus (Step 501), an alarm is displayed on the operating unit 19 (Step 502). The operator reads the content of the alarm and prepares the reagent bottles for the analysis items required to be exchanged, and inputs the requested information for removing the reagent bottles from the operating unit 19. Corresponding to the request information, the signal generating unit 16 outputs a bottle removing request signal to the control unit 17. The control unit 17 stops the operation of pipetting of a sample after that time using the sample pipetter 6, and continues to perform reaction and analysis for samples having been pipetted to complete the analysis operation (step 503).

After completion of the operation of pipetting reagents in regard to the analysis item of the on going process using the reagent pipetters 5a and 5b, the control unit 17 moves the bottle holders 4a, 4b so that each of the reagent bottles on the outer and inner bottle holders 4a, 4b in regard to the same analysis item approaches the bottle exchanging area 10 (Step 504). After movement is stopped, the lid 11 is opened (Step 505). The operator takes out the first reagent bottle and the second reagent bottle for the analysis item to be removed from the bottle holders 4a, 4b and sets a new first reagent bottle and a new second reagent bottle to the bottle holders 4a, 4b. When the lid 11 is closed with an operator's instruction after exchanging the bottles (Step 506), the control unit 17 starts the identifying information reading operation. Initially, identifying information of a reagent bottle set in the outer peripheral row is read (Step 507), and the light transmitting portion 8 is moved in front of the reading unit 7 (Step 508), and then the identifying information of the reagent bottle set in the inner peripheral row is read (Step 509). The processes of Step 504 to Step 509 are repeated for the number of analysis items required to be exchanged. When the exchanging operation is completed (Step 510), the control unit 17 re-starts the operation of each of the units of the analysis apparatus to perform the analyzing operation for each analysis item according to an operator's instruction.

The method of reading the reagent information is the same as that for setting the reagent bottles described above. The reagent bottle is moved in front of the reagent information reading unit 7 to read the reagent information every time the reagent bottle is exchanged, the reagent information is read by the reagent information reading unit 7 arranged in the bottle exchanging area 10 every time the reagent bottle is exchanged, or the reagent information is read together after all the reagent bottles needed to be exchanged have been exchanged.

Figure 7:
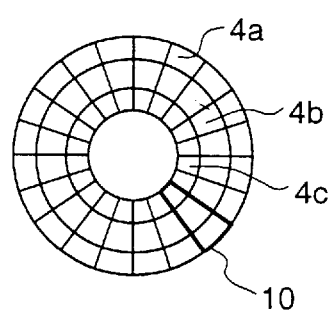
FIG. 7 is a view showing a first alternative embodiment of a reagent containing device.
Figure 8:
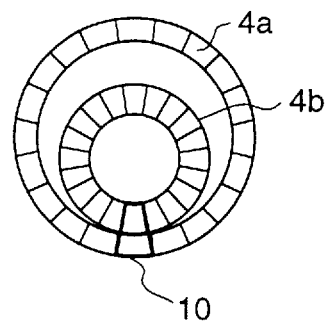
FIG. 8 is a view showing a second alternative embodiment of a reagent containing device.
Figure 9:
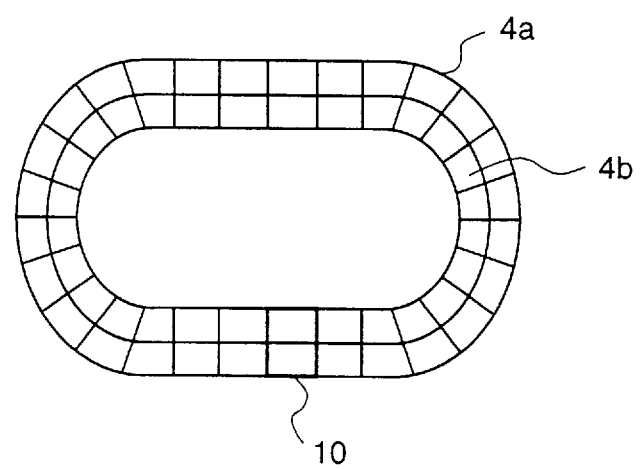
FIG. 9 is a view showing a third alternative embodiment of a reagent containing device.

FIG. 7 to FIG. 9 show alternative embodiments of arrangements of the outer and the inner bottle holders 4a, 4b.

In the embodiment of FIG. 7, independently movable bottle holders 4a, 4b, 4c are arranged three-fold, and it is also possible to arrange them four-fold. These arrangements are effective means for improving the process capacity when three kinds of reagents or four kinds of reagents are required for one analysis item. In such a case having an increased number of reagent bottle rows, the operator is required to pay attention to the various positions since there are three or four rows of the reagent bottles. Therefore, in such a case, it is very effective to employ a multiple reagent bottle row type and arrange the bottle exchanging area in one place.

In the embodiment of FIG. 8, the outer bottle holder 4a and the inner bottle holder 4b have different rotating centers, and both of the rings of the bottle holders approach each other at the position of the bottle exchanging area 10. In this case, it is possible to improve the cooling efficiency by conducting the cooling recirculation water in the gap between the inner periphery and the outer periphery. It is also possible to make the whole apparatus small in size by improving the space efficiency by arranging the pipetters in the gap.

In the embodiment of FIG. 9, the reagent bottles are connected using a chain or the like to be circulated. In this case, the structure becomes complex, but there is an advantage in that the space efficiency is further improved. Furthermore, the three arrangements of FIG. 7 to FIG. 9 may be combined.

Figure 10:
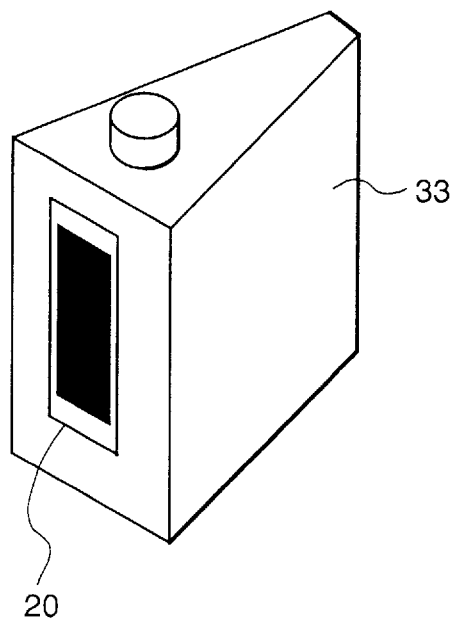
FIG. 10 is a perspective view showing an embodiment of a reagent bottle.
Figure 11:
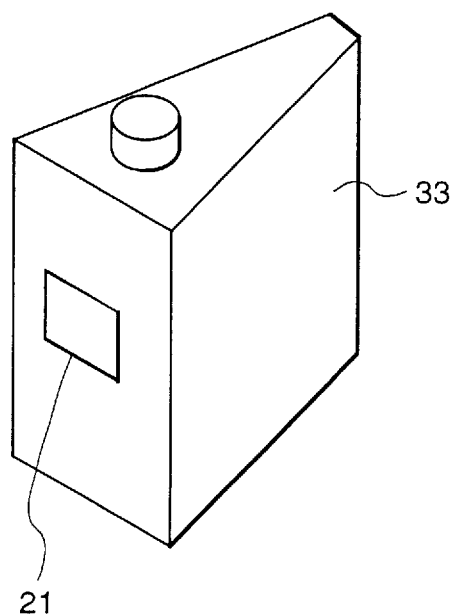
FIG. 11 is a perspective view showing another embodiment of a reagent bottle.

FIG. 10 and FIG. 11 show embodiments of methods of displaying reagent information or reagent bottles. In FIG. 10, a bar code label 20 is attached onto the surface of the reagent bottle 33. The embodiment of FIG. 10 is employed in the embodiment of FIG. 1. In FIG. 11, an information medium 21 such as an IC chip is attached onto the reagent bottle 33.

Figure 12:
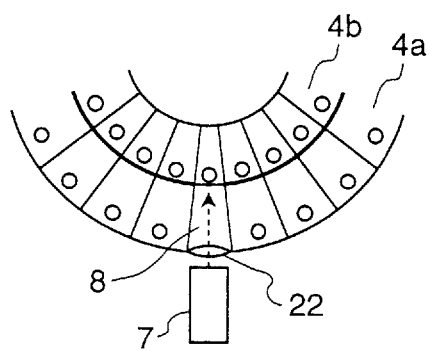
FIG. 12 is a view showing a first alternative embodiment of a reagent information reading means.
Figure 13:
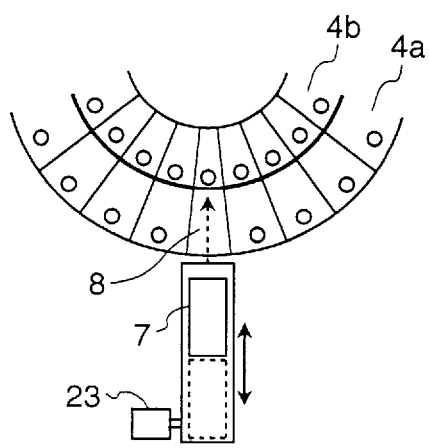
FIG. 13 is a view showing a second alternative embodiment of a reagent information reading means.
Figure 14:
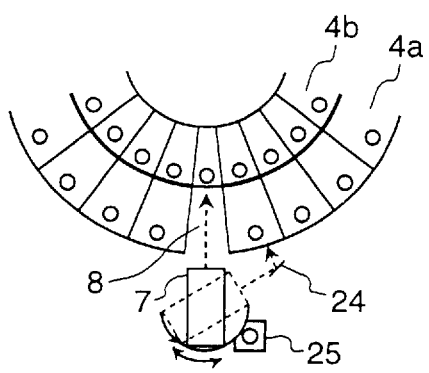
FIG. 14 is a view showing a third alternative embodiment of a reagent information reading means.

FIG. 12 to FIG. 14 show alternative embodiments of reagent information reading means. The embodiment of FIG. 12 is effective for a bar code reader 7 having a shallow readable depth, and a lens 22 is provided in the light transmitting portion 8. In the embodiment of FIG. 13, a bar code reader 7 is moved back and forth to the light transmitting portion 8 by a drive unit 23. In the embodiment of FIG. 14, a reflection mirror 24 is arranged near the outer bottle holder 4a, and a bar code reader 7 is rotated by a rotating mechanism 25, and thereby the bar code in the outer peripheral row is read though the mirror 24 and the bar code in the inner peripheral row is directly read.

In a case where the cover 9 has no room to install the lid 11 and the drive unit 13, instead of providing the lid and the drive unit, a mechanism for locking the cover 9 in the closing state, a detector for detecting an opening state of the cover 9 and a detector for detecting a closing state of the cover 9 are provided and controlled. Instead of providing the opening 10 of the cover 9, a light producing diode can be provided for indicating a bottle exchanging area where a reagent bottle to be exchanged or an empty position is controlled so as to be positioned, and thereby an operator may be informed of the position of the reagent bottle to be exchanged. The operation of such an embodiment will be described below.

In Step 412 of FIG. 4 and Step 505 of FIG. 5, the releasing operation of the lock is performed instead of the opening operation of the lid 11, and the opening of the cover 9 is detected instead of detection the opening of the lid 11, and the closing of the cover 9 is detected instead of the detection of the closing of the lid 11. The operator instructs the closure of the cover 9 after completion of the setting or exchanging of reagent bottles, and then the next operation is started after confirmation of the cover 9 having been closed.

The volume of the first reagent is generally more than the volume of the second reagent, and the volume of the first reagent is often four to five times as much as the volume of the second reagent in the case of analysis having a large analyzing frequency. Of course, there are some cases where the volume of the first reagent exceeds the range depending on the method of analysis and due to the characteristics of the reagent (preservability, solubility and the like). The reason why the volume of the first reagent is generally more than the volume of the second reagent is that since calorimetric analysis strongly depends on temperature, the first reagent is pipetted and the reaction solution is heated to adjust its condition, and at a certain time, for example five minutes, after the second reagent for starting the reaction is pipetted.

What is claimed is:

1. An analyzer comprising a means for pipetting samples from sample containers to reaction containers on a reaction line, a means for pipetting reagents from reagent bottles in a reagent containing device to said reaction containers, and a means for analyzing reaction solutions in said reaction containers, wherein said reagent containing device comprises an outer bottle holder and an inner bottle holder each of which has reagent bottle receiving positions arranged in a loop-shape, a first driving means for circularly driving said outer bottle holder, and a second driving means for circularly driving said inner bottle holder; and said analyzer further comprises a control means for controlling said first and second driving means to position a first reagent bottle on the outer bottle holder and a second reagent bottle on the inner bottle holder for the same analysis item as an analysis item of said first reagent bottle at a predetermined bottle exchanging area by driving said outer and said inner bottle holders corresponding to requesting information on removing reagent bottles.

2. An analyzer according to claim 1, wherein said control means positions an empty reagent bottle receiving position on said outer bottle holder and an empty bottle receiving position on said inner bottle holder at said bottle exchanging area by driving said outer and said inner bottle holders corresponding to requesting information on receiving reagent bottles.

3. An analyzer according to claim 2, which further comprises:

a reading means for reading identifying information attached onto the bottles set on said outer and said inner bottle holders; and a memory means for storing the read identifying information with related positional information on the set bottles.

4. An analyzer according to claim 3, wherein said outer bottle holder comprises a window for reading identifying information of bottles set on the inner bottle holder; and said reading means reads the identifying information of bottles set on the inner bottle holder while said outer bottle holder is stopped so that said window for reading faces said reading means.

5. An analyzer according to claim 1, wherein said reagent containing device comprises a cover for covering said outer and said inner bottle holders; and said cover comprises an opening corresponding to said bottle exchanging area and a lid for opening and closing said opening.

* * * * *